United States Patent [19]

Kanayama

[11] 4,390,664
[45] Jun. 28, 1983

[54] PROCESS FOR PREPARING A POLYEPOXIDE AND COMPOSITION THEREFROM

[75] Inventor: Kaoru Kanayama, Ami, Japan

[73] Assignee: Mitsubishi Petrochemical Co., Ltd., Tokyo, Japan

[21] Appl. No.: 335,813

[22] Filed: Dec. 30, 1981

[30] Foreign Application Priority Data

Feb. 27, 1981 [JP] Japan .................. 56-26770

[51] Int. Cl.³ ............................................. C08G 59/32
[52] U.S. Cl. ...................................... 525/117; 528/98;
528/104; 525/482; 525/504; 525/507
[58] Field of Search .................. 528/98, 103, 104;
525/507, 117, 482, 504

[56] References Cited

U.S. PATENT DOCUMENTS 3,860,561 1/1975 Vargia et al. .................. 525/507
4,137,220 1/1979 Lazzerini et al. ................ 525/507

Primary Examiner—Earl A. Nielsen
Attorney, Agent, or Firm—Oblon, Fisher, Spivak, McClelland & Maier

[57] ABSTRACT

A curable epoxy resin composition of substantially improved curing time and high temperature properties comprising a polyepoxide of the formula:

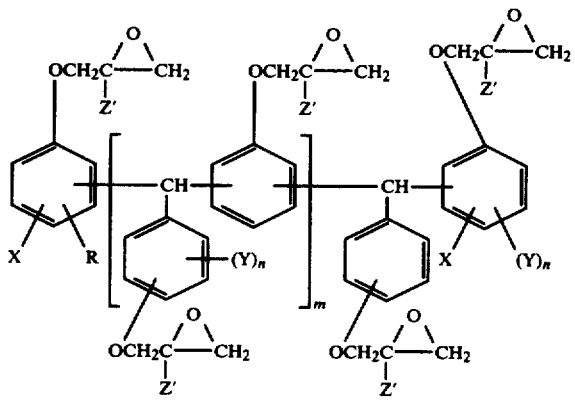

wherein R is H or an alkyl of up to about 18 carbon atoms, X is H or halogen, Y is an alkyl of up to about 18 carbon atoms or methoxy, Z' is H or $CH_3$, m is an integer of not less than 1, n is an integer of up to 2, and from about 25 to about 120 parts by weight, per 100 parts by weight of the polyepoxide, of an epoxy resin hardener.

11 Claims, 2 Drawing Figures

PROCESS FOR PREPARING A POLYEPOXIDE AND COMPOSITION THEREFROM

BACKGROUND OF THE INVENTION

1. Field of the Invention

The present invention relates to a process for preparing a polyepoxide which can be cured in a short time by an epoxy resin hardener. The present polyepoxides are used for casting materials, varnishes, impregnants, bonding agents, sealing materials, powdered paints, fiber-resin composites, laminates, molding compounds, and the like with an epoxy resin hardener.

2. Description of the Prior Art

Because epoxy resins exhibit superior insulation properties, adhesiveness, high-temperature properties, corrosion inhibiting properties and mechanical strength, the resins are commonly used in many applications, for example, potting, encapsulating, coating, foaming, casting, caulking, molding, adhesives, tooling, and the like. In the manufacture of computors and small calculating instruments the electrical parts are sealed with an epoxide resin. For such applications the polyepoxide should be cured for a short time and give a cured product having superior high-temperature properties.

Several polyepoxides have been used in these applications, and they include a polyglycidylethernovolak resin ("Epicoat 154" available from Yuka Shell Epoxy Kabushiki Kaisha), a polyglycidylether-cresol-novolak resin ("EOCN" available from Nippon Kayaku Co., Ltd.), methylene-di-aniline-tetraepoxides, and polyepoxides of tri- or tetra-(hydroxyphenyl)alkanes. The cured products obtained from these polyepoxides have superior high-temperature properties, but these polyepoxides cure only over long periods of time.

It is also known that polyepoxides of tris(4-hydroxyphenyl)methane, the so called "Leucaurin Epoxides", can be cured with an epoxy resin hardener such as an aromatic amine, a polycarboxylic anhydride, or the like. The resulting product has a heat distortion temperature of more than 300° C. (see U.S. Pat. No. 3,787,451). However, it takes sixteen hours to cure at 180° C. A need therefore continues to exist for a polyepoxide material which rapidly cures while providing excellent physical and mechanical characteristics.

SUMMARY OF THE INVENTION

Accordingly, one object of the present invention is to provide a polyepoxide which is curable in a short time with an epoxy resin hardener with the resulting cured product demonstrating a high heat distortion temperature.

Briefly, this and other objects of the present invention as hereinafter will become more readily apparent can be attained by a curable polyepoxide of formula (I)

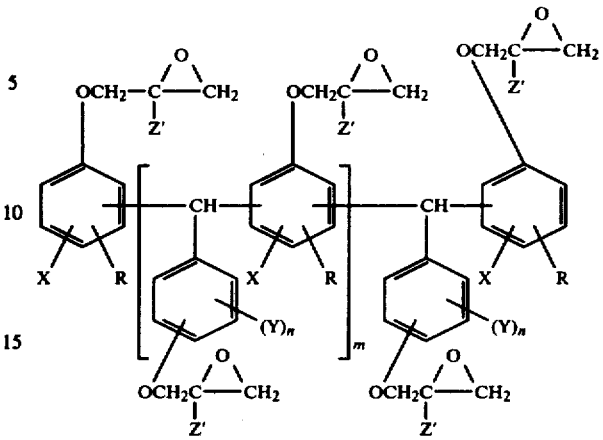

wherein R is H or an alkyl of up to about 18 carbon atoms; X is H or halogen; Y is an alkyl of up to about 18 carbon atoms or methoxy; Z' is H or CH$_3$; m is an integer not less than 1; and n is 0, 1 or 2.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
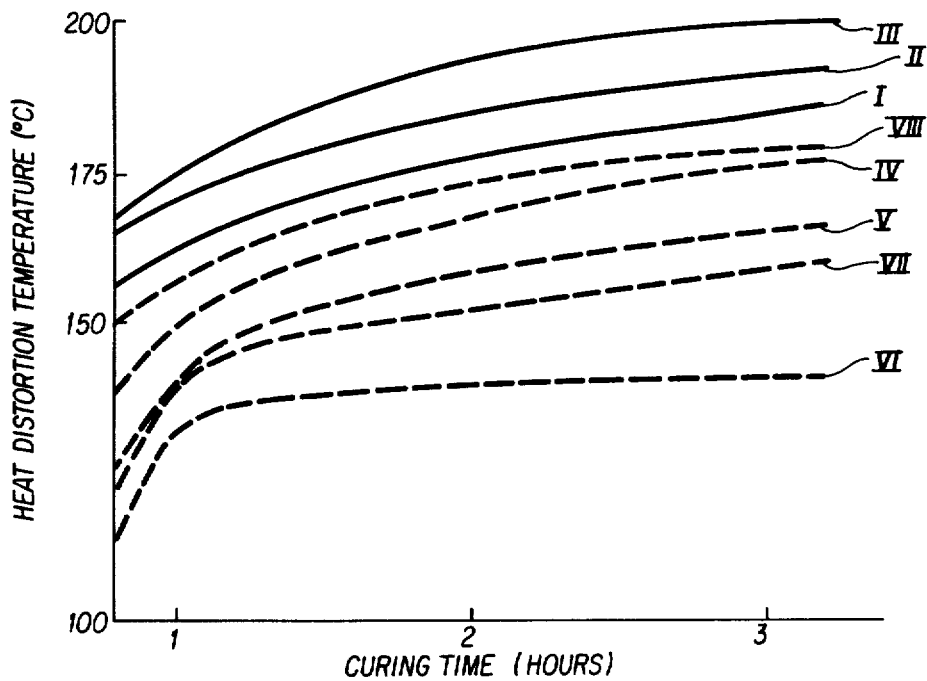
FIG. 1 shows the curing times of several polyepoxide compositions in relation to the heat distortion temperature.

The process of the present invention comprises reacting a polyhydric phenol compound of formula (II)

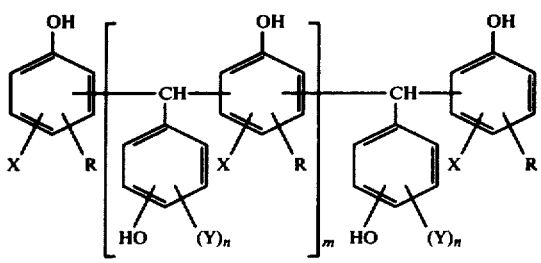

wherein R, X, Y, m and n are the same as defined in formula (I), with an epihalohydrin or epimethylhalohydrin of formula (III)

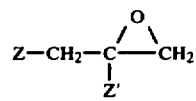

wherein Z is chlorine or bromine and Z' is H or CH$_3$.

The polyhydric phenol corresponding to the above formula (II) is obtained by reacting one mole of a phenol or derivative thereof represented by formula (IV)

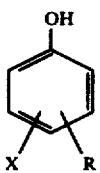

wherein R is H or an alkyl of up to 18 carbon atoms and X is H or a halogen atom, with 0.1–3.0 moles, preferably 0.3–1.5 moles of an aromatic aldehyde represented by formula (V)

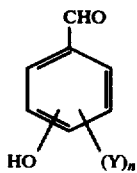

wherein Y is an alkyl of up to about 18 carbon atoms or methoxy and n is 0, 1 or 2.

The polymerization reaction is carried out in the presence of an acidic catalyst, for instance, a mineral acid such as hydrochloric acid, sulfuric acid, or the like; an organic acid such as p-toluene sulfonic acid, oxalic acid and a catalyst for a novolak resin, the reactants being heated to a temperature of from 80° to 250° C., preferably 100° to 180° C., for about from one to six hours.

Suitable phenols having the above formula (IV) include phenol, ortho-cresol, meta-cresol, para-cresol, ortho-bromophenol, meta-bromophenol, para-bromophenol, propyl phenol, butyl phenol, octyl phenol, nonyl phenol, and the like. These phenols can be used independently or in combination. Suitable aromatic aldehydes corresponding to the above formula (V) include hydroxybenzaldehyde, 4-hydroxy-3-methoxybenzaldehyde (so-called "vanillin"), hydroxy-di-methoxybenzaldehyde, salicylaldehyde, and the like.

In the polymerization reaction, about 0.1–about 5 parts by weight of the acidic catalyst is used per 100 parts by weight of the phenols represented by formula (IV).

The resulting polyhydric phenol compound prepared by the polymerization reaction is a mixture of at least 50% by weight of the polyhydric phenol represented by formula (II) and less than 50% by weight of a polyhydric phenol which is represented by formula (VI)

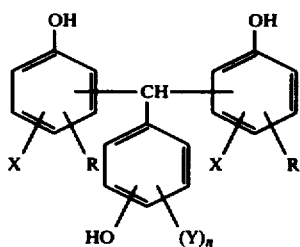

wherein R, X, Y and n are the same as in formula (II).

The molecular weight of the resulting polyhydric phenol compound is from about 500 to about 3,000 and its softening point ranges from about 80° C. to about 180° C.

Suitable epihalohydrin or methyl-epihalohydrin compounds represented by formula (III) include epichlorohydrin, epibromohydrin, 1-chloro-2,3-epoxy-2-methylpropane, and the like. Preferably, epichlorohydrin is used.

The polyepoxides of formula (I) of the present invention can be prepared, for example, by processes (A) and (B).

Process (A)

The present polyepoxide can be prepared by reacting a polyhydric phenol represented by formula (II) with an epihalohydrin or methylepihalohydrin represented by formula (III) in the presence of an etherification catalyst for the polyhydric phenol and epihalohydrin at a temperature of 50° C. to 150° C. (the first step), and then reacting the reaction product with an alkali metal hydroxide at a temperature of 35° C. to 80° C. (the second step).

In process (A), at least 3 moles, per hydroxyl equivalent of the phenol, of the epihalohydrin or methylepihalohydrin is used.

The etherification catalyst which is used for the reaction between the phenol compound and epihalohydrin or methylepihalohydrin in the first-step of process A may be any catalyst known to catalyze the reaction. Suitable catalysts include tertiary phosphines and quaternary phosphonium compounds such as triphenylphosphine, tributyl phosphine, tetraphenyl phosphonium chloride and the like; organic sulfides and sulfonium compounds such as dibutyl sulfide, diisopropyl sulfide, trimethyl sulfonium iodide, triphenyl sulfonium bromide and the like; betaine compounds; and tertiary amines such as triethylamine, N,N'-dimethylaniline, benzyldimethylamine, benzyltrimethyl-ammonium chloride and the like. Superior catalysts are quaternary ammonium compounds such as tetramethyl ammonium chloride, tetraethyl ammonium chloride and tetramethyl ammonium bromide. In particular, tetramethyl ammonium chloride and tetramethyl ammonium bromide are advantageous because of their low costs and high catalytic activities. Advantageously, the etherification catalyst is added in an amount of 0.002 to 0.5 mole % based on the phenolic hydroxyl groups.

The second-step of the reaction (closed ring reaction) of process A is conducted at a temperature of 35° C. to 80° C., preferably 50° C. to 70° C. A suitable amount of the alkali metal hydroxide (MOH) is at least 1 mole per mole of the epihalohydrin. Suitable alkali metal hydroxides include sodium hydroxide and potassium hydroxide. The alkali metal hydroxide can be used in the form of a solid.

The first step of the reaction is conducted for at least 5 minutes, preferably for 1–3 hours, and the second-step of the reaction is conducted for at least 15 minutes, preferably for 1–10 hours. There is no particular upper limit to the reaction period, but too long a reaction time is unnecessary and uneconomical.

The first and second steps of the reactions can be conducted in the presence of an inert organic solvent such as methyl isobutyl ketone, methyl ethyl ketone or toluene.

Process (B)

The present polyepoxide can be prepared by reacting a polyhydric phenol of formula (II) with excess epihalohydrin or methylepihalohydrin of formula (III), adding an aqueous solution of an alkali metal hydroxide dropwise at a temperature of 110° C. to 125° C., preferably at reflux, and removing the water immediately by azeotropic distillation for at least 90 minutes, preferably about 2-6 hours. Suitable alkali metal hydroxides which can be used include sodium hydroxide. The concentration of alkali metal hydroxide in the aqueous solution is about 50% by weight. The amount of the alkali metal hydroxide used is at least 1 mole, preferably 1.05 to 1.5 moles, per hydroxy equivalent of the phenol. The epihalohydrin or methylepihalohydrin is used in an amount of at least 3 moles per hydroxyl equivalent of the phenol. The reaction can be performed in excess epihalohydrin as the solvent.

The polyepoxide prepared by process A or B can be purified and isolated, for example, by (1) filtering the reaction mixture using a filter aid such as cellite to remove an alkali metal halide such as sodium chloride, and evaporating off the excess epihalohydrin; or by (2) dissolving the reaction mixture in a water insoluble or sparingly water-soluble organic solvent such as methyl isobutyl ketone, or toluene, contacting the solution with water or warm water to dissolve the inorganic impurities in the aqueous layer, and distilling the excess epihalohydrin and organic solvent to obtain the polyepoxide.

The resulting epoxidation reaction product has a mean average molecular weight of from 700 to 5,000 (the mean average of subscript m in formula (I) is from about 1.2 to about 1.5), an epoxy value of from 130 to 280, and a softening point of from 40° C. to 140° C. This product principally contains the polyepoxide of formula (I) and small amounts of a polyglycidyl ether of an alkoxy-substituted tri(hydroxyphenyl) methane or triepoxides of leucaurin as shown by formula (I) wherein m is 0.

The polyepoxide thus prepared is admixed prior to curing with an epoxy resin hardener. If necessary, it may be admixed with other epoxides to form epoxide blends with desirable properties.

Suitable epoxy resin hardeners used in this invention include:

(1) amino compounds having at least one hydrogen atom attached to the nitrogen atom, for instance, diethylenetriamine, triethylenetetramine, xylylenediamine, m-phenylenediamine, diaminodiphenylmethane, 2,6-diaminopyridine, N-methylmorpholine, tetraethylenepentamine, triethylenediamine, tetramethylguanidine, 4-picoline, tributylamine, benzylmethylamine, tris(dimethylaminomethyl)-phenol, imidazole, pyridine, triethanolamine, dicyandiamide, $BF_3$, amine salts, diaminodiphenylsulfone, anilineformaldehyde resins; adducts of one of these compounds and an epoxy-group-containing compound, acrylonitrile, an acrylic acid ester or the like; polyamide amines derived from an aliphatic polyamine and a dimer of an unsaturated aliphatic fatty acid and the like;

(2) polycarboxylic acids or anhydrides thereof such as phthalic anhydride, hexahydrophthalic anhydride, methyl-endo-methylene-tetrahydrophthalic anhydride, maleic anhydride, dodecenylsuccinic anhydride, methyl hexahydrophthalic anhydride, pyromellitic anhydride, glutaric anhydride, benzophenonetetracarboxylic anhydride, cyclopentanoictetracarboxylic anhydride, and the like;

(3) phenol compounds such as for instance, novolak, alkyl phenol novolaks such as cresol novolak, butyl phenol novolak, nonylphenol novolak, and polyalkenyl phenols such as poly-para-vinylphenol, and poly-para-isopropenylphenol.

The hardener is generally used in an amount of from about 25 to about 120 parts by weight per 100 parts by weight of the polyepoxide, but this amount can be appropriately changed as needed. The hardener is preferably used in an equivalent amount per epoxy equivalent of the polyepoxides.

In combination with the above-mentioned hardeners, curing accelerators can be used.

Suitable accelerators include quaternary ammonium salts such as tetraethylammonium chloride, tetraethylammonium bromide, cetyltrimethylammonium chloride, and the like; tertiary amines such as benzyldimethylamine, triethylamine, 2,4,6-(tris-dimethylaminoethyl)-phenol, and the like; amine hardening catalysts such as 2-methyl-4-methylimidazole, 2-phenylimidazole, 1-benzyl-2-methylimidazole, 2-ethyl-4-methylimidazoleazine, imidazoleazines containing 11 carbon atoms (not including hexamethylene tetramine); lithium salts such as lithium chloride, lithium bromide, lithium iodide, and the like. These accelerators are normally used in an amount of 1-10% by weight of the polyepoxide used.

Other epoxides can be admixed with the present polyepoxide to improve the workability of the composition when the hardener is admixed therewith or to improve the heat-temperature properties of the cured product. Suitable epoxides which can be admixed with the polyepoxide include glycidyl ethers of polyhydric phenols; glycidyl ethers of diphenylol alkanes, e.g. 2,2-bis(4-hydroxyphenyl)propane, 1,1-bis(4-hydroxyphenyl)ethane and bis(4-hydroxyphenyl)methane; glycidyl ethers of 4,4'-dihydroxydiphenylsulfone, hydroquinone, resorcinol, dihydroxyphenyl or dihydroxynaphthalene; glycidyl ethers of novolak or resole condensates of formaldehyde and polyhydric phenols or cresols, poly(epoxyalkyl) ethers of aliphatic polyhydroxy compounds, e.g., epoxy compounds derived from ethylene glycol, glycerol, trimethylolpropane and pentaerythritol; polyglycidyl ethers of polycarboxylic acids, e.g., phthalic acid, terephthalic acid, adipic acid, tetrahydrophthalic acid, or hexahydrophthalic acid; polyglycidyl esters of polyunsaturated aliphatic acids, e.g., the diglycidyl ester of linolenic acid dimer; epoxidized esters of unsaturated acids, e.g., epoxidized linseed oil or soybean oil; diepoxidized butadiene, epoxidized vinylcyclohexane, 3,4-epoxycyclohexyl methyl ester of 3,4-epoxycyclohexane carboxylic acid; polyglycidyl isocyanurate; diglycidylaniline; copolymers of styrene and glycidyl methacrylate; copolymers of acrylonitrile and glycidyl methacrylate; copolymers of styrene and arylglycidyl ethers; or mixtures thereof.

These epoxides are also commercially available under various trademarks, such as "Epikote 828" (manufactured by Shell Chemical), "Epikote 815" (manufactured by Shell Chemical), "Araldite GY260" (manufactured by Ciba Geigy), or "D.E.R. 330" (manufactured by Dow Chemical), "Epikote 154" (manufactured by Shell Chemical), "Araldite EPN 1138" (manufactured by Ciba Geigy), "Araldite ECN 1235" (manufactured by Ciba Geigy), and the like.

Monofunctional reactive diluents can also be admixed with the combination of the polyepoxide and another epoxide. The diluents include, for instance, styrene oxide, cyclohexene oxide, phenyl glycidyl ether, butyl glycidyl ether, allyl glycidyl ether, glycidyl ether of versatic acid and the like. Mixing of the polyepoxide and the hardener is conducted with an extruder, mil rolls, kneader or the like.

A curable epoxy resin composition comprising the polyepoxide of formula (I) and the hardener can generally be cured at a temperature in the range of about 60° C. to about 300° C., preferably 100° C.–250° C.

The time required for curing varies depending upon the curing temperature and the like, but normally, the curing time can be appropriately selected within a range of about 1 minute to about 20 hours, preferably about 5 minutes to 5 hours.

Compared with the curing time of Leucaurin triepoxide, the curing time of the polyepoxide of formula (I) is much shorter, while giving a cured product which has the same heat distortion temperature (see FIG. 1 and compare diagram I with diagram V).

The present cured epoxy resin products demonstrate superior high-temperature properties and mechanical strength.

The present curable epoxy resin composition is especially useful in the electrical field.

Having generally described this invention, a further understanding can be obtained by reference to certain specific examples which are provided herein for purpose of illustration only and are not intended to be limiting unless otherwise specified.

Run 1

In a three-necked flask equipped with a thermometer, an agitator and a reflux condenser, were placed 188 grams of phenol, 152 grams of vanillin, and 0.3 grams of conc. hydrochloric acid. After the reactant were heated to a temperature of 100° C. for 30 minutes, 0.5 grams of p-toluene sulfonic acid was added. A distillation apparatus was attached to the flask, and the temperature of the reactants was raised to 180° C., and the reaction was allowed to continue for two hours at the same temperature while removing excess amounts of phenol by distillation.

After completion of the reaction, 500 grams of methyl isobutyl ketone was added to dissolve the reaction mixture. The resulting mixture was neutralized with 500 grams of 3% aqueous solution of $NaHCO_3$, and washed with 1,000 grams of distilled water to remove the catalyst. The methyl isobutyl ketone and the unreacted phenol were removed by distillation under a reduced pressure of from 1.0 mmHg to 100 mmHg to yield 279.4 grams of a dark brown resin.

The resin is a polyphenol having the following properties.
Softening point: 116° C.–126° C.
Hydroxy equivalent: 112 (according to the acetylchloride method)
Residual phenol: 0.4% by weight (by gas chromatography)

Analysis by gel permeation chromatography (GPC) indicated 68% by weight of polyphenol of formula (II) wherein m is not less than 1. Further details of the composition of the resin are shown in Table 1.

Run 2

The same procedure as described in Run 1 was repeated except that the amount of phenol was 564 grams (molar ratio of phenol to vanillin is 6). There was obtained 291 grams of a pale red resin having the following properties.
Softening point: 80° C.–90° C.
Hydroxy equivalent: 110

Analysis by GPC indicated 36.6% by weight of the polyphenol of formula (II) wherein m is not less than 1. Further details of the composition of the resin are shown in Table 1.

Run 3

The same procedure as described in Run 1 was repeated except that 122 grams of p-hydroxybenzaldehyde was used in place of vanillin. There was obtained 253.3 grams of a resin having the following properties.
Softening point: 75° C.–85° C.
Hydroxy equivalent: 106

Analysis by GPC indicated 57% by weight of the polyphenol of formula (II) wherein m is not less than 1. Further details of the composition of the resin are shown in Table 1.

Run 4

The same procedure as described in Run 1 was repeated except that 122 grams of salicylaldehyde was used in place of vanillin. There was obtained 250.9 grams of a resin having the following properties. P0 Softening point: 80° C.–90° C.
Hydroxy equivalent: 108

Analysis by GPC indicated 60.8% by weight of the polyphenol of formula (II) wherein m is not less than 1. Further details of the composition of the resin are shown in Table 1.

Run 5

This run duplicates the procedure of preparing 4,4',4''-hydroxy-3-methoxyphenyl methane described in U.S. Pat. No. 3,787,451. This compound is represented by formula (II) wherein m is 0.

To a solution of vanillin (100 g) and phenol (61.1 g) in glacial acetic acid (600 ml.), chilled to 4° C., was slowly added with stirring, a sulfuric acid/glacial acetic acid (100 ml./300 mg.) catalyst solution (precooled to 4° C.).

The resulting solution was stirred for an additional 30 minutes, then stored at 4° C. for a period of 3 days.

Addition of water (2.5 liter) to the reaction solution yielded a suspension of solids that was dissolved and extracted with diethyl ether. The organic phase was neutralized with aqueous $NaHCO_3$ and washed several times with saturated sodium chloride solution.

Ether and most of the unreacted phenol was removed by distillation under reduced pressure. The solid product mass was crushed in water, filtered, washed with fresh water and dried. The yield was 131.8 g (63%) of dried product having a melting point of 68° C.–73° C.

Analysis by GPC indicated by 88.7% by weight of 4,4'4''-hydroxy-3-methoxyphenyl methane of formula (II) wherein m is 0.

TABLE 1

| Composition* | (% by weight) Run | | | | |
|---|---|---|---|---|---|
| | 1 | 2 | 3 | 4 | 5 |
| Trinuclear compound (m = 0) | 32.0 | 63.4 | 43.0 | 39.2 | 88.7 |
| Pentanuclear compound (m = 1) | 14.3 | 20.2 | 11.6 | 16.1 | 10.2 |
| Heptanuclear compound (m = 2) | 8.0 | 11.3 | 7.9 | 10.4 | 1.1 |
| Nonanuclear compound (m = 3) | 45.7 | 5.1 | 37.5 | 34.3 | 0 |

*The numbers in parenthesis indicates the value of m in formula (II). For instance, the trinuclear compound is a polyphenol of formula (II) wherein m is 0.

EXAMPLE 1

In a three-necked flask equipped with a thermometer, an agitator and a reflux condensor, 112 grams of the polyphenol obtained in Run 1, 740 grams of epichlorohydrin and 1.1 grams of tetraethylammonium chloride were added. The solution was heated to reflux (about 117° C.) in an oil-bath for two hours to complete the coupling reaction.

The resulting solution was chilled to a temperature of about 60° C. and then reacted for two hour at 50° C.-70° C. under a reduced pressure of 40 mmHg-100 mmHg with 42 grams of NaOH after a device to separate water was attached to the flask. In the reaction, product water was removed as an azeotrope with non-reacted epichlorohydrin by distillation under reduced pressure.

After 2.5 liters of methyl isobutyl ketone was added to the obtained epichlorohydrin solution containing polyepoxides, the solution was washed repeatedly with water to remove product NaCl and unreacted NaOH, neutralized with 3% phosphoric acid, and the lower aqueous layer was separated and removed.

The upper methyl isobutyl ketone layer was removed by distillation at a temperature of from about 60° C. to 150° C. under a reduced pressure of from about 100 mmHg to about 0.1 mmHg to yield 201.6 grams of a red brown polyepoxide.

The obtained polyepoxide had the following properties.

Epoxy value: 210
Softening point: 85° C.-95° C. EXAMPLES 2-3 and COMPARATIVE EXAMPLES 1-2

The same procedures as described in Example 1 were repeated except that the polyphenols obtained in Runs 2-5 were used in place of the phenol obtained in Run 1.

Polyepoxides having the properties shown in Table 2 were obtained.

obtained from the cured products made of the following epoxides.

I. Polyepoxide obtained from Example 1
II. Polyepoxide obtained from Example 2
III. Polyepoxide obtained from Example 3
IV. Polyepoxide obtained from Comparative Example 1
V. Polyepoxide obtained from Comparative Example 2
VI. Polyepoxide of the phenol-novolak: "Epikote 154" (Trade mark of Yuka Shell Eoxy K.K.)
VII. Polyepoxide of the cresol-novolak "ECON 104-S" (Trade mark of Nippon Kayaku Corporation)
VIII. Methylenediamine tetraepoxides "YH 434" (Trademark of Tohto Kasei K.K.)

As can be seen from FIG. 1, especially the comparison of diagrams I and V, it is evident that the composition of this invention can be cured in a short time to yield a cured product having superior hightemperature properties.

Experiment 2

To 100 parts by weight of the polyepoxide used in 1, 25 parts by weight of methylene dianiline and 250 parts by weight of pulverulent silica were added. The resulting mixture was heated to a temperature of 60° C.-80° C., kneaded for ten minutes with rollers, and then crushed. The crushed mixture was cast into a press mold and was compressed under a pressure of 100 kg/cm$^2$ at a temperature of 160° C. for ten minutes to yield a cured product with a size of 5 inches×¼ inches×¼ inches. The obtained product had the heat distortion temperature (ASTM-D-648) shown in Table 3.

TABLE 2

|  |  | Example 1 | Comparative Example 1 | Example 2 | Example 3 | Comparative Example 2 |
|---|---|---|---|---|---|---|
| Polyphenol | Obtained by Run No. | 1 | 2 | 3 | 4 | 5 |
|  | Amount used (grams) | 112 | 110 | 106 | 108 | 100 |
| Product | Yield (grams) | 201.6 | 184 | 188 | 178 | 160.3 |
|  | Epoxy value | 210 | 207 | 200 | 197 | 201 |
|  | Softening point (°C.) | 85–95 | 67–77 | 60–70 | 55–65 | 56–66 |

Cured Product

Experiment 1

One hundred (100) parts by weight of the polyepoxide obtained in Example 1, 80 parts by weight of methyl nadic anhydride (1 equivalent methyl nadic anhydride/equivalent of polyepoxide) available from Nippon Kayaku Co. Ltd., and one part by weight of 2-ethyl-4-methylimidazole available from Shikoku Chemical Corporation were mixed at a temperature of about 150° C.

The molten mixture was poured into a casting mold and cured at 150° C.

The correlation between heat distortion temperature (HDT) and curing time for the cured product is shown in FIG. 1.

In the same way as described above, the polyepoxides obtained in Examples 2-3, Comparative Examples 1-2 and several epoxides available on the market were cured.

Correlations between HDT and curing time for several cured products are shown in FIG. 1. The curves labeled by numbers 1-VIII in FIG. 1 represent the data

TABLE 3

| Polyepoxide | HDT |
|---|---|
| Polyepoxide obtained from Example 1 | more than 300° C. |
| Polyepoxide obtained from Example 2 | more than 300° C. |
| Polyepoxide obtained from Example 3 | more than 300° C. |
| Polyepoxide obtained from Comparative Example 1 | 300° C. |
| Polyepoxide obtained from Comparative Example 2 | 291° C. |
| Epikote 154 | 205° C. |
| EOCN 104-S | 216° C. |
| YH 434 | 259° C. |

Figure 2:
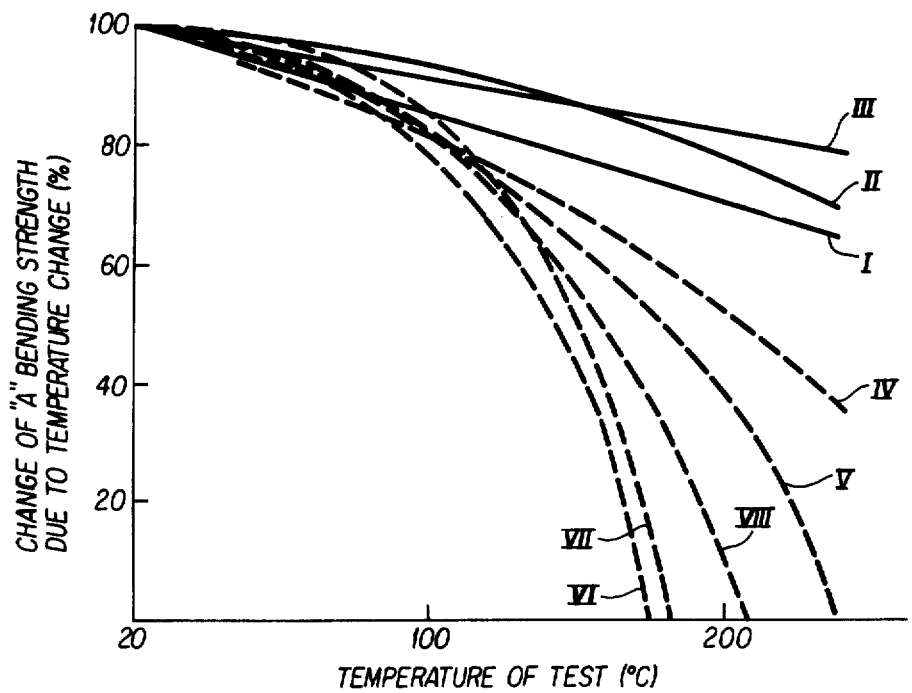
FIG. 2 shows the bending strength of cured epoxides versus temperature.

The bending strengths of the cured products were measured in accordance with ASTM D-648. The results are shown in FIG. 2, and it is evident that the composition of the present invention can be cured at 106° C. for ten minutes to yield a product which exhibits a very small change with changes in temperature.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing a polyepoxide of the formula:

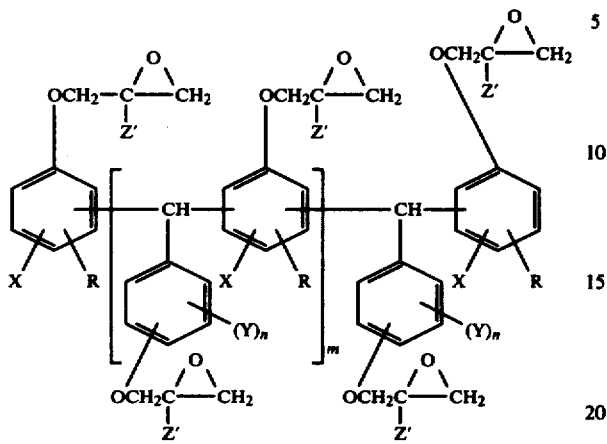

wherein R is H or an alkyl of up to about 18 carbon atoms, X is H or halogen, Y is an alkyl of up to about 18 carbon atoms or methoxy, Z' is H or CH₃, m is an integer of not less than 1; n is 0, 1 or 2, which comprises:

reacting a polyhydric phenol of the formula:

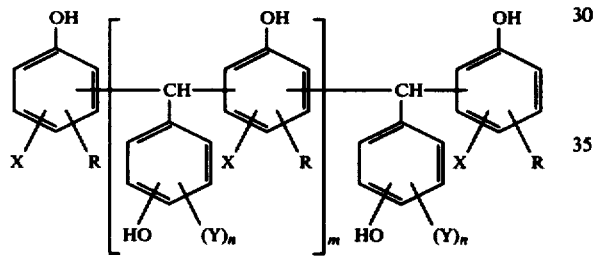

wherein R, X, Y, m and n are the same as defined above and an epihalohydrin or methylepihalohydrin of the formula:

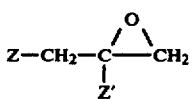

wherein Z represents halogen and Z' represents H or CH₃.

2. The process of claim 1, wherein the reaction is conducted in the presence of an aqueous solution of an alkali metal hydroxide at a temperature of 110° C. to 125° C.

3. The process of claim 1, wherein the reaction of the polyhydric phenol and epihalohydrin or methylepihalohydrin is first conducted in the presence of an etherification catalyst at a temperature of 50° C. to 150° C., and then an alkali metal hydroxide is added to the reaction product to perform a closed ring reaction at a temperature of 35° C. to 80° C.

4. The process of claim 2 or 3, wherein the polyhydric phenol contains less than 50 mole % of a polyphenol represented by the formula:

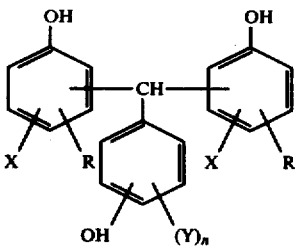

wherein R is H or an alkyl of up to about 18 carbon atoms, X is H or halogen, Y is an alkyl of up to about 18 carbon atoms or methoxy and n is 1 or 2.

5. The process of claim 3, wherein the etherification catalyst is a quaternary ammonium compound.

6. A curable epoxy resin composition of substantially improved curing time and high temperature properties, comprising:

a polyepoxide of the formula:

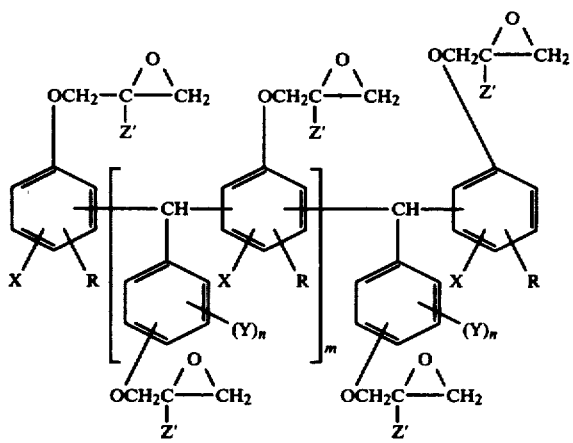

wherein R is H or an alkyl of up to about 18 carbon atoms, X is H or halogen, Y is an alkyl of up to about 18 carbon atoms or methoxy, Z' is H or CH₃, m is an integer of not less than 1, n is an integer of up to 2, and from about 25 to about 120 parts by weight, per 100 parts by weight of the polyepoxide, of an epoxy resin hardener.

7. The composition of claim 6, wherein said hardener is present in an amount of one equivalent per epoxy equivalent in the polyepoxide.

8. The composition of claim 6, wherein the mean average of m expressed by formula (I) is from about 1.2 to about 1.5.

9. The composition of claim 6, wherein said resin hardener is an amino compound having at least one hydrogen atom attached to the nitrogen atom, a polycarboxylic acid or a phenol compound.

10. The composition of claim 6, wherein said composition further comprises from 1-10% by weight of a curing accelerator based on the polyepoxide.

11. The composition of claim 6, wherein said composition further comprises an epoxide compound selected from the group consisting of glycidyl ethers of polyhydric alcohols, glycidyl ethers of diphenylol alkanes, glycidyl ethers of 4,4'-dihydroxydiphenylsulfone, glycidyl ethers of novolak or resole condensates of formaldehyde and polyhydric phenols or cresols, poly(epoxyalkyl) ethers of aliphatic polyhydroxy compounds, polyglycidyl esters of polycarboxylic acids, polyglycidyl esters of polyunsaturated aliphatic acids, epoxidized esters of unsaturated acids, diepoxidized butadiene, epoxidized vinylcyclohexane, 3,4-epoxycyclohexyl methyl ester of 3,4-epoxycyclohexane carboxylic acid, polyglycidyl isocyanurate, diglycidylaniline, copolymers of styrene and glycidyl methacrylate, copolymers of acrylonitrile and glycidyl methacrylate, copolymers of styrene and arylglycidyl ethers and mixtures thereof.

* * * * *